US012636328B2

(12) United States Patent
Sohn et al.

(10) Patent No.: US 12,636,328 B2
(45) Date of Patent: May 26, 2026

(54) PROBIOTICS COMPLEX COMPOSITION WITH IMMUNOMODULATORY AND IMMUNE HOMEOSTASIS PROPERTY

(71) Applicant: LACTOMASON CO., LTD., Jinju-si (KR)

(72) Inventors: Minn Sohn, Jinju-si (KR); Je Seong Park, Gwangju-si (KR); So Lim Shin, Anyang-si (KR); Ye Ji You, Siheung-si (KR)

(73) Assignee: LACTOMASON CO., LTD., Jinju-si (KR)

( * ) Notice: Subject to any disclaimer, the term of this patent is extended or adjusted under 35 U.S.C. 154(b) by 38 days.

(21) Appl. No.: 18/785,085

(22) Filed: Jul. 26, 2024

(65) Prior Publication Data

US 2024/0408155 A1 Dec. 12, 2024

Related U.S. Application Data

(63) Continuation of application No. PCT/KR2022/012959, filed on Aug. 30, 2022.

(30) Foreign Application Priority Data

May 26, 2022 (KR) ........................ 10-2022-0064632

(51) Int. Cl.
| A61K 35/747 | (2015.01) |
| A61K 35/00 | (2006.01) |
| A61K 35/745 | (2015.01) |
| A61P 37/02 | (2006.01) |

(52) U.S. Cl.
CPC .......... A61K 35/747 (2013.01); A61K 35/745 (2013.01); A61P 37/02 (2018.01); *A61K 2035/115* (2013.01)

(58) Field of Classification Search
CPC ................ A61K 35/747; A61K 35/745; A61K 2035/115; A61P 37/02; A23L 33/135; C12R 2001/225; C12N 1/20
See application file for complete search history.

(56) References Cited

FOREIGN PATENT DOCUMENTS

| JP | 2019-208486 A | 12/2019 |
| KR | 10-2016-0098118 A | 8/2016 |
| KR | 10-2017-0086109 A | 7/2017 |
| KR | 101847154 B1 | 4/2018 |
| KR | 10-1862051 B1 | 5/2018 |
| KR | 10-1919938 B1 | 2/2019 |
| KR | 10-2136522 B1 | 7/2020 |
| KR | 102317409 B1 | 10/2021 |

OTHER PUBLICATIONS

Dell'Anno M, Callegari ML, Reggi S, Caprarulo V, Giromini C, Spalletta A, Coranelli S, Sgoifo Rossi CA, Rossi L. Animals (Basel). Jun. 12, 2021;11(6):1766. doi: 10.3390/ani11061766. PMID: 34204784; PMCID: PMC8231520. (Year: 2021).*
International Search Report of PCT/KR2022/012959 dated Feb. 22, 2023.
Balance Within™ Immunity on the online product sales page dated Jan. 5, 2021 , 1 6. ULR: https://www.amway.co.kr/shop/nutrition/basic/probioticfibers/p/303426K.
Kim. T. R. et al. Anti inflammatory effects of Lactobacillus reuteri LM1071 via MAP kinase pathway in IL 1β induced HT 29 cells. Journal of Animal Science and Technology. 2020, vol. 62, No. 6, pp. 864-874.
Hwang, Y. P.. et Inhibitory Effects of Lactobacillus plantarum LM1001 on Particulate Matter Induced Liver Injury . The Korean Society for Microbiology and Biotechnology 46 th Annual Meeting & International Symposium . 2019, p. 586 , poster N 32.
Kim, I. et al. Immunomodulatory Effects of β 1,3/1,6 glucan and Lactobacillus plantarum LM1004 on Atopic Dermatitis Models . Journal of Life Science . 2018, vol. 28, No. 1, pp. 17-25.
Matsuguchi , T. et al. Lipoteichoic Acids from Lactobacillus StrainsElicit Strong Tumor Necrosis Factor Alpha Inducing Activities in Macrophages through Toll Like Receptor 2 . Clinical and Diagnostic Laboratory Immunology. Mar. 2003, vol. 10, No. 2, pp. 259-266.
Ya Hu et al. The regulation of nitric oxide in tumor progression and therapy . Journal of International medical research. 202 0, vol. 48, No. 2, pp. 1-9.

* cited by examiner

*Primary Examiner* — Kade Ariani
(74) *Attorney, Agent, or Firm* — NKL LAW; Jae Youn Kim

(57) ABSTRACT

A mixed strain of probiotics having immunoregulatory functions and a composition comprising the same are provided. The composition can regulate immunity by increasing the production amount of NO or inhibiting the excessive production of NO induced by an inflammatory substance. The mixed strain can be applied to food compositions, health functional food compositions, pharmaceutical compositions, and the like.

9 Claims, 12 Drawing Sheets

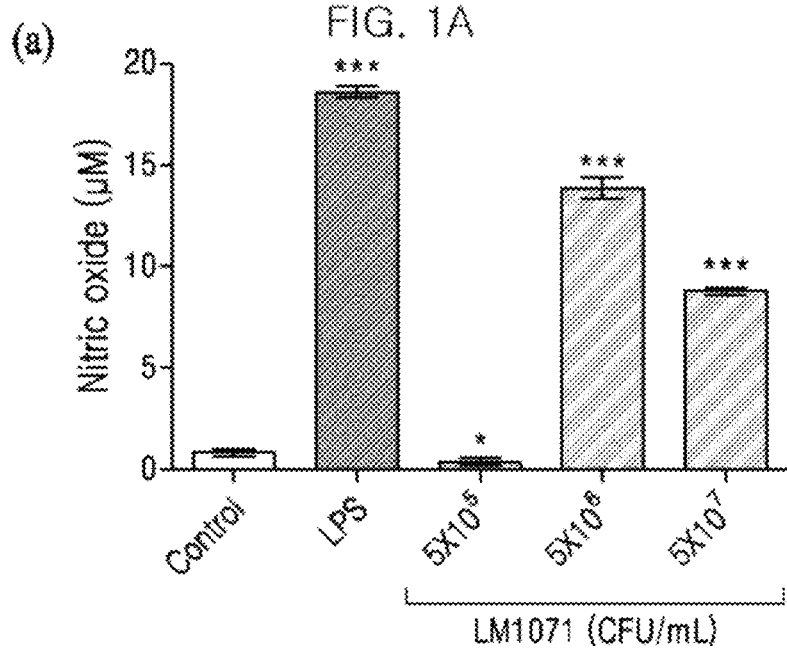
*p<0.05, p<0.01, *p<0.001 against control group.
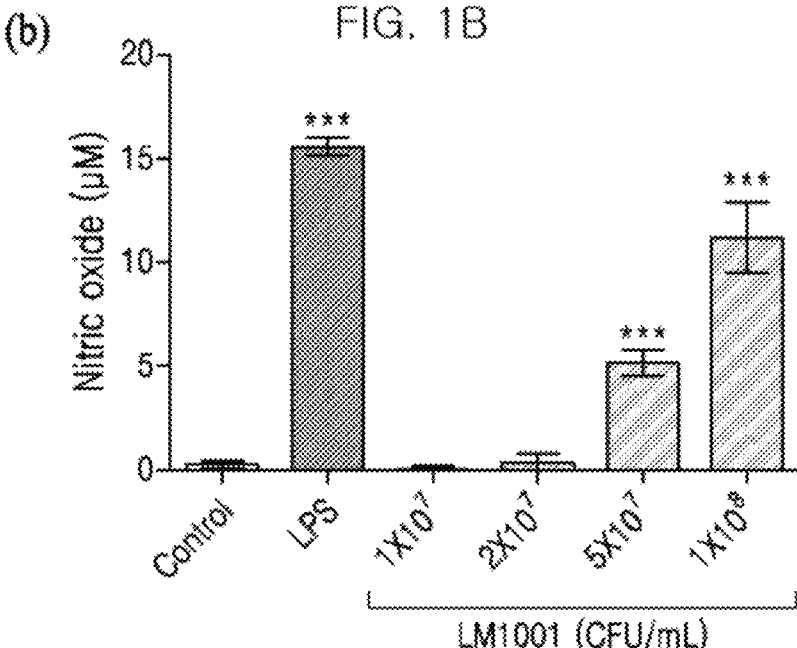
*p<0.05, p<0.01, *p<0.001 against control group.

(a)

*p<0.05, p<0.01, *p<0.001 against LPS group.

(b)

*p<0.05, p<0.01, *p<0.001 against LPS group.

*p < 0.05, p < 0.01, *p < 0.001 against *L. rhamnosus* GG group.

*p < 0.05, p < 0.01, *p < 0.001 against LPS group.

(a)

*p<0.05, p<0.01, *p<0.001 against control group.

*p<0.05, p<0.01, *p<0.001 against control group.

(a)

*p < 0.05, p < 0.01, *p < 0.001 against LPS group.

(b)

*p < 0.05, p < 0.01, *p < 0.001 against LPS group.

*p < 0.05, p < 0.01, *p < 0.001 against LPS group.

*p < 0.05, p < 0.01, *p < 0.001 against LPS group.

(e)

*p < 0.05, p < 0.01, *p < 0.001 against LPS group.

(a)

*p<0.05, p<0.01, *p<0.001 against control group.

(b)

*p<0.05, p<0.01, *p<0.001 against LPS group.

PROBIOTICS COMPLEX COMPOSITION WITH IMMUNOMODULATORY AND IMMUNE HOMEOSTASIS PROPERTY

TECHNICAL FIELD

The present disclosure relates to a mixed strain of probiotics having immunoregulatory functions and a composition comprising the same. Under the provisions of the Budapest Treaty on the International Recognition of the Deposit of Microorganisms for the Purposes of Patent Procedure, the *Bifidobacterium animalis* subsp. *lactis* LM1017 strain was deposited with the international depositary authority: the Korean Culture Center of Microorganisms (KCCM) on Nov. 14, 2019, under the Accession Number: KCCM12629P; the *Bifidobacterium longum* LM1024 strain was deposited with the international depositary authority: the Korean Culture Center of Microorganisms (KCCM) on Dec. 23, 2020, under the Accession Number: KCCM12919P; the *Lactobacillus reuteri* LM1071 strain was deposited with the international depositary authority: the Korean Culture Center of Microorganisms (KCCM) on Dec. 31, 2019, under the Accession Number: KCCM12650P; the *Lactobacillus plantarum* LM1001 strain was deposited with the international depositary authority: the Korean Culture Center of Microorganisms (KCCM) on Nov. 12, 2010, under the Accession Number: KCCM42959; the *Lactococcus lactis* LM1009 strain was deposited with the international depositary authority: the Korean Culture Center of Microorganisms (KCCM) on May 16, 2017, under the Accession Number: KCCM80146; the *Streptococcus thermophilus* LM1012 strain was deposited with the international depositary authority: the Korean Culture Center of Microorganisms (KCCM) on May 30, 2018, under the Accession Number: KFCC11771P; and the *Lactobacillus plantarum* LM1004 strain was deposited with the international depositary authority: the Korean Culture Center of Microorganisms (KCCM) on Oct. 28, 2016, under the Accession Number: KCCM43246.

BACKGROUND

There are many bacteria living in the digestive tract of the human body. The human body has about 10 trillion normal cells but has about 100 trillion bacteria which are about 10-fold greater than the normal cells. Most of these bacteria make up the gut bacterial flora and affect the human body's immune regulation through interaction with various immune cells in the intestine. These bacteria can be divided into beneficial bacteria that help human gut health and harmful bacteria that are harmful to human health. The health of human body can be maintained when beneficial bacteria are more dominant than harmful bacteria, such as *Escherichia coli* (*E. coli*), *Veillonella, Clostridium perfringens*, and microbes living in various digestive tracts maintain a balance.

Immune cells in our bodies help to maintain health by controlling externally invading antigens (including microbes) and abnormal cells produced in the body. More than 70% of these immune cells are in the digestive tracts and control microbes already inhabiting the digestive tracts or externally invading microbes. However, when activation of immune responses by the immune cells is excessive, allergy, rheumatism, atopic dermatitis, asthma, rheumatoid arthritis, lupus, or inflammatory bowel diseases (ulcerative colitis, Crohn's disease, diverticulosis, etc.), diabetes, and the like may occur. Therefore, immunoregulatory ability for maintaining immunological homeostasis by inhibiting excessively activated immune responses is an important physiological function of the immune system to prevent the occurrence of the above-described diseases. T cells among the immune cells can directly remove host cells infected by bacteria or viruses, and particularly, helper T-cells promote the differentiation of other immune cells and induce the activation of the immune cells (cellular and humoral immune responses). The activated immune responses are inhibited by immunoregulatory T-cells (Treg) which are known to play an important role in maintaining immunological homeostasis.

Gut microbes are antigens that cause immune responses in the human body, and may have immune tolerance mechanisms for suppressing immune responses of the human body in order to live in symbiosis with the human body. Some of the gut microbes are known to be involved in the division of T-cells and to induce the differentiation and proliferation of immunoregulatory T-cells in the gut. Novel lactic acid bacteria having immunoregulatory activities derived from human digestive tract and the use thereof (Korean Patent No. 10-1862051) are disclosed as an example of a composition developed for regulating immunity by using such microbes. However, there is still a need for in-depth development and various studies on compositions having excellent effects on immunoregulation.

Accordingly, the present inventors made diligent efforts to develop a composition having excellent immunoregulatory functions and resultantly developed a mixed strain and a composition comprising the mixed strain capable of regulating immunity by increasing the production amount of NO or inhibiting the excessive production of NO induced by an inflammatory substance, and completed the present disclosure.

DISCLOSURE OF THE INVENTION

Problems to be Solved by the Invention

The present disclosure is conceived to provide a mixed strain of probiotics having immunoregulatory functions and a composition comprising the same.

However, the problems to be solved by the present disclosure are not limited to the above-described problems. Although not described herein, other problems to be solved by the present disclosure can be clearly understood by a person with ordinary skill in the art from the following descriptions.

Means for Solving the Problems

A first aspect of the present disclosure provides a mixed strain having immunoregulatory functions.

A second aspect of the present disclosure provides a food composition for regulating immunity, comprising a mixed strain having immunoregulatory functions as an active ingredient.

A third aspect of the present disclosure provides a pharmaceutical composition for preventing or treating immunoregulation-related diseases, comprising a mixed strain having immunoregulatory functions as an active ingredient.

Effects of the Invention

A composition comprising a mixed strain having immunoregulatory functions as an active ingredient according to an embodiment of the present disclosure can regulate immunity by increasing the production amount of NO or inhibiting the excessive production of NO induced by an inflammatory substance. The mixed strain can be applied to food compositions, health functional food compositions, pharmaceutical compositions, and the like.

BRIEF DESCRIPTION OF THE DRAWINGS

FIG. 1A shows the production amount of NO (immune-boosting ability) when treated with a strain LM1071 alone according to an embodiment of the present disclosure.

FIG. 1B shows the production amount of NO (immune-boosting ability) when treated with a strain LM1001 alone according to an embodiment of the present disclosure.

BEST MODE FOR CARRYING OUT THE INVENTION

Figure 2A:
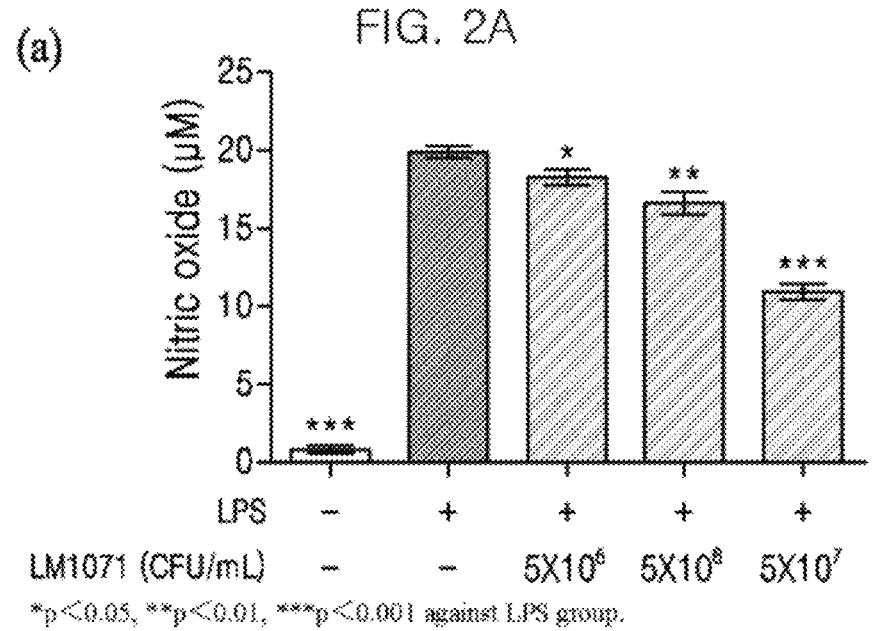
FIG. 2A shows the inhibition of production of NO induced by LPS (anti-inflammatory ability) when treated with the strain LM1071 alone according to an embodiment of the present disclosure.

Hereafter, examples of the present disclosure will be described in detail with reference to the accompanying drawings so that the present disclosure may be readily implemented by a person with ordinary skill in the art. However, it is to be noted that the present disclosure is not limited to the examples but can be embodied in various other ways.

In the drawings, parts irrelevant to the description are omitted for the simplicity of explanation, and like reference numerals denote like parts through the whole document.

Through the whole document, the term 'comprises or includes' and/or 'comprising or including' used in the document means that one or more other components, steps, operation and/or existence or addition of elements are not excluded in addition to the described components, steps, operation and/or elements unless context dictates otherwise.

Through the whole document, the term 'combination(s) of' included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Hereinafter, embodiments and examples of the present disclosure will be described in detail with reference to the accompanying drawings. However, the present disclosure may not be limited to the following embodiments, examples, and drawings.

A first aspect of the present disclosure provides a mixed strain having immunoregulatory functions.

Through the whole document, the term "immunoregulatory function" refers to immune-boosting ability and anti-inflammatory ability. That is, in the present disclosure, the expression "having immunoregulatory functions" refers to having both of "immune-boosting ability" and "anti-inflammatory ability".

In an embodiment of the present disclosure, the mixed strain may contain *Lactobacillus reuteri* LM1071 (KCCM12650P) and *Lactobacillus plantarum* LM1001 (KCCM42959), but may not be limited thereto.

In an embodiment of the present disclosure, the mixed strain may further contain *Bifidobacterium animalis* subsp. *lactis* LM1017 (KCCM12629P), *Bifidobacterium longum* LM1024 (KCCM12919P), *Lactococcus lactis* LM1009 (KCCM80146), *Streptococcus thermophilus* LM1012 (KFCC11771P), and *Lactobacillus plantarum* LM1004 (KCCM43246) in addition to the *Lactobacillus reuteri*

LM1071 (KCCM12650P) and the *Lactobacillus plantarum* LM1001 (KCCM42959), but may not be limited thereto.

In an embodiment of the present disclosure, the mixed strain can regulate immunity by increasing the production amount of NO or inhibiting the excessive production of NO induced by an inflammatory substance and thus can maintain immunological homeostasis.

Through the whole document, the term "NO (nitric oxide)" refers to a compound in which nitrogen is oxidized, which is called "nitrogen oxide" or "nitrogen monoxide". It is formed from arginine, which is an amino acid, in cells, and serves as a kind of signal transmitter and is involved in various physiological activities such as immune reaction, vasodilation and signal transmission. It is also known to induce inflammation and pain by promoting the secretion of inflammatory cytokines such as TNF-α and IL-6 (Hu et al., 2020).

In an embodiment of the present disclosure, the inflammatory substance may include one or more selected from the group consisting of LPS, zymosan, concanavalin A, bacteria, viruses, parasites, mycetes, and allergens, but may not be limited thereto.

In an embodiment of the present disclosure, the mixed strain may regulate immunity. Specifically, the mixed strain may be contained in various compositions such as food compositions, health functional food compositions, pharmaceutical compositions, and the like.

A second aspect of the present disclosure provides a food composition for regulating immunity, comprising a mixed strain having immunoregulatory functions as an active ingredient. The features described above in respect of the first aspect of the present disclosure may equally apply to the food composition according to the second aspect of the present disclosure.

In an embodiment of the present disclosure, the composition can regulate immunity. Specifically, the composition can regulate immunity by increasing the production amount of NO or inhibiting the excessive production of NO induced by an inflammatory substance.

In an embodiment of the present disclosure, the composition may contain the mixed strain, live bacteria, heat-killed bacteria, cultured products, fragments and/or extracts thereof.

In an embodiment of the present disclosure, the composition may contain *Lactobacillus reuteri* LM1071 (KCCM12650P) and *Lactobacillus plantarum* LM1001 (KCCM42959), but may not be limited thereto.

In an embodiment of the present disclosure, the composition may further contain *Bifidobacterium animalis* subsp. *lactis* LM1017 (KCCM12629P), *Bifidobacterium longum* LM1024 (KCCM12919P), *Lactococcus lactis* LM1009 (KCCM80146), *Streptococcus thermophilus* LM1012 (KFCC11771P), and *Lactobacillus plantarum* LM1004 (KCCM43246) in addition to the *Lactobacillus reuteri* LM1071 (KCCM12650P) and the *Lactobacillus plantarum* LM1001 (KCCM42959), but may not be limited thereto.

Through the whole document, the term "heat-killed bacteria" is opposite to the term "live bacteria" and refers to bodies obtained by suppressing the growth of bacteria such as heat-treating live bacteria obtained by fermentation and metabolites thereof. The heat-killed bacteria may contain cytoplasm, cell wall, antibacterial substances such as bacteriocin, polysaccharides, organic acid, and the like. Products using the heat-killed bacteria have higher stability than live bacteria products and are particularly excellent in heat resistance and have high stability to the external environment. Therefore, the products using the heat-killed bacteria are easier to store and have longer shelf life than the existing live bacteria products. Further, since the regulations on the use of antibiotics become stricter, there are a handful of companies that have produced heat-killed bacteria products. Therefore, considering the application as substitutes and the number of the producing companies, the marketability and growth potential is very high.

Through the whole document, the term "cultured product" refers to a substance obtained by culturing the strain of the present disclosure in a known liquid medium or solid medium and may be interchangeably used with "culture fluid".

Through the whole document, the term 'food' may include meats, sausages, breads, chocolates, candies, snacks, cookies, pizza, ramens, other noodles, gums, dairy products including ice cream, soups, beverages, teas, drinks, alcohol drinks, vitamin complexes, health functional foods and health foods, and may include all foods in the accepted meaning.

Through the whole document, the term 'health functional food' refers to foods prepared and processed using raw materials or ingredients having useful functions to the human body in accordance with the Health Functional Food Act, No. 6727, and the 'functionality' refers to adjusting nutrients on a structure and a function of the human body or obtaining a useful effect for health such as a physiological action.

The food of the present disclosure can be manufactured by conventional methods used in the art, and can be manufactured by adding conventional raw materials and ingredients used in the art. Further, a formulation of the food is not limited as long as the formulation is accepted as a food. The food composition of the present disclosure may be prepared in a variety of formulations. Since the food is used as raw materials, unlike general drugs, the food composition is free from side effects which may occur when a drug is taken for a long time and may have excellent portability.

The health functional food refers to a food having effects of actively maintaining or promoting health conditions, as compared with general foods, and a health supplement food refers to a food for supplementing health. If necessary, the health functional food, health food and health supplement food may be interchangeably used with each other. Specifically, the health functional food is a food prepared by adding the strain(s) of the present disclosure such as beverages, teas, spices, gums, confectionery, etc., or prepared in a capsule, a powder, or a suspension form. The health functional food means that it has a specific effect on health when consumed, but unlike general drugs, the health functional food is free from side effects that may occur when a drug is taken for a long time since the food is used as raw materials.

Since the food of the present disclosure could be consumed on a daily basis, a high effect can be expected to improve depression, so it can be very useful.

The food composition may further contain a physiologically acceptable carrier. The kind of the carrier is not particularly limited. Any carrier may be used as long as it is commonly used in the art.

Further, the food composition may further contain additional ingredients that are commonly used in food compositions so as to improve smell, taste, visuality, etc. For example, the food composition may contain vitamins A, C, D, E, B1, B2, B6, B12, niacin, biotin, folate, pantothenic acid, etc. Furthermore, the food composition may also contain minerals such as zinc (Zn), iron (Fc), calcium (Ca), chromium (Cr), magnesium (Mg), manganese (Mn), copper (Cu), chromium (Cr), etc. In addition, the food composition may contain amino acid such as lysine, tryptophan, cysteine, valine, etc.

Further, the food composition may also contain food additives, such as preservatives (potassium sorbate, sodium benzoate, salicylic acid, sodium dehydroacetate, etc.), disinfectants (bleaching powder, higher bleaching powder, sodium hypochlorite, etc.), antioxidants (butylhydroxyanisole (BHA), butylhydroxytoluene (BHT), etc.), colorants (tar color, etc.), color-developing agents (sodium nitrite, etc.), bleaching agents (sodium sulfite), seasonings (monosodium glutamate (MSG), etc.), sweeteners (dulcin, cyclemate, saccharin, sodium, etc.), flavors (vanillin, lactones, etc.), swelling agents (alum, potassium D-bitartrate, etc.), fortifiers, emulsifiers, thickeners (adhesive pastes), film-forming agents, gum base agents, antifoaming agents, solvents, improvers, etc. The additives may be selected and used in an appropriate amount depending on the type of food.

The mixed strain of the present disclosure may be added as it is or may be used in conjunction with other foods or food ingredients, and may be appropriately used according to a conventional method. The mixing amount of active ingredients may be appropriately determined depending on the purpose of use (prophylactic, health, or therapeutic treatment). In general, when a food or a beverage is manufactured, the food composition of the present disclosure may be added in an amount of 50 parts by weight or less, specifically 20 parts by weight or less based on the total weight of the food or the beverage. However, when taken for the purpose of health and hygiene, the food composition may be contained in an amount below the range. In addition, since there is no safety problem, the active ingredients may be used in an amount above the range.

The food composition of the present disclosure may be used as, for example, a health beverage composition, and in this case, the health beverage composition may further contain various flavors or natural carbohydrates, as in common beverages. The natural carbohydrates may include monosaccharides such as glucose and fructose; disaccharides such as maltose and sucrose; polysaccharides such as dextrin and cyclodextrin; and sugar alcohols such as xylitol, sorbitol and erythritol. The sweeteners may be natural sweeteners such as thaumatin or a *stevia* extract; or synthetic sweeteners such as saccharin or aspartame. The natural carbohydrate may be generally used in an amount of from about 0.01 g to about 0.04 g, and specifically, from about 0.02 g to about 0.03 g based on 100 mL of the health beverage composition of the present disclosure.

In addition, the health beverage composition may contain various nutrients, vitamins, minerals, flavors, colorants, pectic acid and salts thereof, alginic acid and salts thereof, organic acid, protective colloidal thickeners, pH regulators, stabilizers, antiseptics, glycerin, alcohols, or carbonating agents. Moreover, the health beverage composition may contain fruit flesh used to prepare natural fruit juices, fruit juice beverages or vegetable beverages. These ingredients may be used individually or in combination. A proportion of the additives is not critical, but is generally selected from 0.01 part by weight to 0.1 part by weight per 100 parts by weight of the health beverage composition of the present disclosure.

The food composition of the present disclosure may contain the mixed strain of the present disclosure in a variety of % by weight as long as it can exhibit the effect of improving the gut environment. Specifically, the mixed strain of the present disclosure may be contained in an amount of 0.00001% by weight to 100% by weight or 0.01% by weight to 80% by weight based on the total weight of the food composition, but may not be limited thereto.

In an embodiment of the present disclosure, the food composition may be a health functional food composition.

A third aspect of the present disclosure provides a pharmaceutical composition for preventing or treating immuno-regulation-related diseases, comprising a mixed strain having immunoregulatory functions as an active ingredient. The features described above in respect of the first and second aspects of the present disclosure may equally apply to the pharmaceutical composition according to the third aspect of the present disclosure.

In an embodiment of the present disclosure, the composition may contain the mixed strain, live bacteria, heat-killed bacteria, cultured products, fragments and/or extracts thereof.

In an embodiment of the present disclosure, the composition may contain *Lactobacillus reuteri* LM1071 (KCCM12650P) and *Lactobacillus plantarum* LM1001 (KCCM42959), but may not be limited thereto.

In an embodiment of the present disclosure, the composition may further contain *Bifidobacterium animalis* subsp. *lactis* LM1017 (KCCM12629P), *Bifidobacterium longum* LM1024 (KCCM12919P), *Lactococcus lactis* LM1009 (KCCM80146), *Streptococcus thermophilus* LM1012 (KFCC11771P), and *Lactobacillus plantarum* LM1004 (KCCM43246) in addition to the *Lactobacillus reuteri* LM1071 (KCCM12650P) and the *Lactobacillus plantarum* LM1001 (KCCM42959), but may not be limited thereto.

Through the whole document, the term "treat" refers to all activities reducing or alleviating symptoms of an immune-related disease by administering a pharmaceutical composition containing the mixed strain of the present disclosure as an active ingredient to a subject with the immune-related disease.

In an embodiment of the present disclosure, the composition can prevent or treat immune-related diseases. Specifically, the composition can prevent or treat immune-related diseases by increasing the production amount of NO or inhibiting the excessive production of NO induced by an inflammatory substance.

Through the whole document, the term "immune-related diseases" refers to various diseases caused by bacterial and viral infections in an immunocompromised state and all of diseases related to autoimmune diseases and allergic responses which may be caused by excessive immune responses.

Through the whole document, the term "immune deficiency" refers to all of diseases caused by dysfunction of components of the immune system, and may include severe combined immunodeficiency (SCID), acquired immune deficiency syndrome (AIDS), and the like.

Through the whole document, the term "hyperimmune diseases" refers to all of diseases caused by over-expression of immunity, and may include autoimmune diseases, such as rheumatoid arthritis, allergy, atopy, and the like.

In an embodiment of the present disclosure, the pharmaceutical composition may be used in the form of oral formulations, such as powders, granules, tablets, capsules, suspensions, emulsions, syrups, aerosols, and the like, external preparations, suppositories, or sterile injectable solutions according to respective conventional methods, but may not be limited thereto.

In an embodiment of the present disclosure, the pharmaceutical composition may be formulated with generally used diluents or excipients such as fillers, bulking agents, binders, wetting agents, disintegrating agents or surfactants, but may not be limited thereto.

In an embodiment of the present disclosure, solid formulations for oral administration may include tablets, pills, powders, granules or capsules, and these solid formulations may be prepared by mixing a heat-killed bacteria derived from the strain with at least one of excipients such as starch, calcium carbonate, sucrose, lactose, or gelatin. Except for the simple excipients, lubricants such as magnesium stearate or talc may be used, but the present disclosure may not be limited thereto.

In an embodiment of the present disclosure, liquid formulations for oral administration may include suspensions, solutions for internal use, emulsions and syrups, and may contain various excipients such as wetting agents, sweeteners, aromatics and preservatives in addition to generally used simple diluents such as water and liquid paraffin, but may not be limited thereto.

In an embodiment of the present disclosure, formulations for parenteral administration may include sterilized aqueous solutions, water-insoluble excipients, suspensions, emulsions, lyophilized preparations, and suppositories, but may not be limited thereto. For example, the water insoluble excipients or suspensions may contain propylene glycol, polyethylene glycol, vegetable oil such as olive oil, injectable ester such as ethyloleate, and the like, but may not be limited thereto. For example, the suppositories may contain witepsol, macrogol, tween 61, cacao butter, laurin butter, glycerol, gelatin, and the like, but may not be limited thereto.

The pharmaceutical composition according to an embodiment of the present disclosure may be a drug composition or a quasi-drug composition.

Through the whole document, the term "quasi-drug" refers to an article having a milder action than drugs, among articles being used for the purpose of diagnosis, treatment, improvement, alleviation, handling or prevention of human or animal diseases. For example, according to the Pharmaceutical Affairs Law, the quasi-drugs are those, excluding articles used as drugs, including articles used for the purpose of treating or preventing human or animal diseases and articles which have a mild action on or have no direct influence on the human body.

The quasi-drug composition of the present disclosure may be manufactured in a formulation selected from the group consisting of body cleanser, sanitizer, detergent, kitchen cleanser, detergent for cleaning, toothpaste, mouthwash, wet wipe, cleanser, soap, hand soap, hair cleanser, hair softener, humidifying filler, mask, ointment or filter filler, but may not be limited thereto.

In an embodiment of the present disclosure, the pharmaceutical composition may be administered in a pharmaceutically effective amount. Through the whole document, the term "pharmaceutically effective amount" refers to an amount sufficient to treat or prevent diseases at a reasonable benefit/risk ratio applicable to any medical treatment or prevention. An effective dosage level may be determined depending on factors including severity of the disease, drug activity, a patient's age, body weight, health conditions, gender, sensitivity to the drug, administration time, administration route, and excretion rate of the composition of the present disclosure, duration of treatment, drugs blended with or co-administered with the composition of the present disclosure, and other factors known in the medical field. The pharmaceutical composition of the present disclosure may be administered individually or in combination with an ingredient known for treating intestinal diseases. It is important to administer an amount to obtain a maximum effect in a minimum amount without side effects by considering all of the above-described factors.

In an embodiment of the present disclosure, an administration dose of the pharmaceutical composition may be determined by a person with ordinary skill in the art in view of purpose of use, severity of the disease, a patient's age, body weight, gender, medical history, or the kind of a material used as an active ingredient. For example, the pharmaceutical composition of the present disclosure may be administered at a dose of from about 0.1 ng/kg to about 1,000 mg/kg, and preferably, from about 1 ng/kg to about 100 mg/kg per adult, and the administration frequency of the composition of the present disclosure is not particularly limited, but the composition may be administered once a day or several times a day in divided doses. The administration dose or the administration frequency does not limit the scope of the present disclosure in any aspect.

The pharmaceutical composition of the present application may be administered via, but not particularly limited to, intraperitoneal administration, intravenous administration, intramuscular administration, subcutaneous administration, intradermal administration, transdermal patch administration, oral administration, intranasal administration, intrapulmonary administration, rectal administration, etc. depending on the purpose. However, when the pharmaceutical composition is administered via oral administration, it can be administered in an unformulated form, and since the strain (s) of the present disclosure can be denatured or degraded by gastric acid, the composition for oral administration may be coated with an active drug, formulated to be protected from degradation in the stomach, or formulated in the form or an oral patch. Also, the composition may be administered by any device capable of delivering an active ingredient to a target cell.

MODE FOR CARRYING OUT THE INVENTION

Hereinafter, the present disclosure will be explained in more detail with reference to Examples. However, the following Examples are illustrative only for better understanding of the present disclosure, but do not limit the present disclosure.

EXAMPLES

Example 1. Test for Immune-Boosting Ability and Anti-Inflammatory Ability when Treated with Each of LM1071 and LM1001 Alone (1) Test for Immune-Boosting Ability A DMEM medium (Welgene, Korea) made of 10% fetal bovine serum (FBS) (Welgene, Korea) and penicillin/streptomycin (Welgene, Korea) was used to culture RAW 264.7 cells, which are a murine macrophage cell line. The RAW 264.7 cells were seed in a 96-well plate at a concentration of $3\times10^4$ cells/well and then cultured overnight (O/N) in a 37° C., $CO_2$ incubator. After the medium was removed from each well, LM1071 or LM1001 was diluted to each bacterial count in the medium and used for treatment for 24 hours. Herein, LPS was used for treatment of a positive control. The production amount of NO was measured with a Griess Reagent system from Promega, and 50 $\mu\ell$ of the cultured medium was transferred into a new 96-well plate. An NO standard solution was used after dilution to a concentration of 1.56 μM to 100 μM to generate an NO standard curve. Then, 50 $\mu\ell$ of a sulfanilamide solution was put into each well and allowed to react for 5 minutes at room temperature protected from light. Further, 50 $\mu\ell$ of an N-1-naphtylethylenediamine dihydrochloride (NED) solution was added to each well and allowed to react for 5 minutes at room temperature protected from light. Then, the absorbance at 540 nm was measured with a microplate reader, and the production amount of NO was calculated based on the NO standard curve (see FIG. 1A, FIG. 1B).

According to the test result, it was confirmed that both LM1071 and LM1001 increase the production amount of NO.

(2) Test for Anti-Inflammatory Ability

Figure 2B:
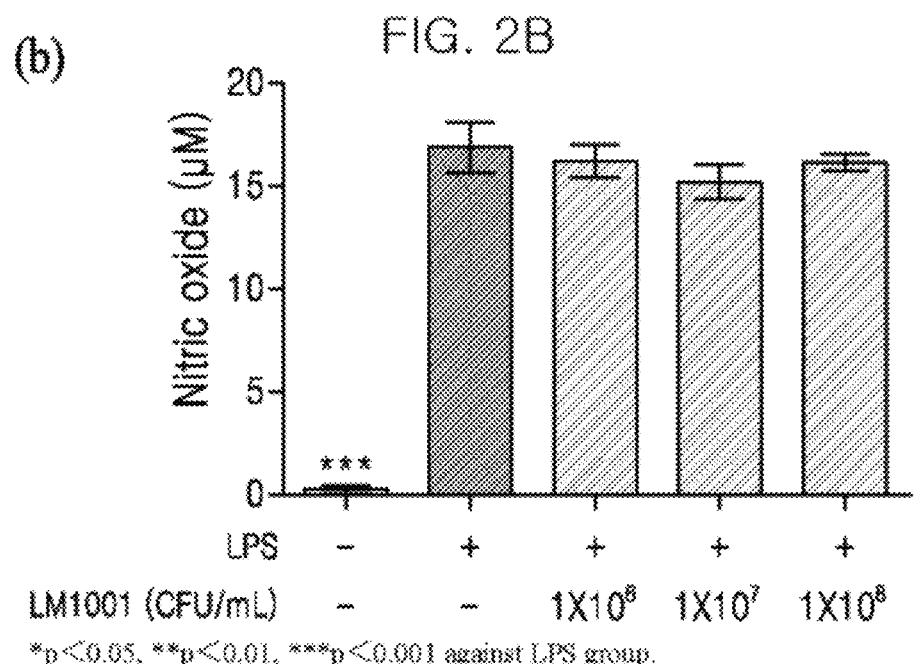
FIG. 2B shows the inhibition of production of NO induced by LPS (anti-inflammatory ability) when treated with the strain LM1001 alone according to an embodiment of the present disclosure.

A DMEM medium (Welgene, Korea) made of 10% fetal bovine serum (FBS) (Welgene, Korea) and penicillin/streptomycin (Welgene, Korea) was used to culture RAW 264.7 cells, which are a murine macrophage cell line. The RAW 264.7 cells were seed in a 96-well plate at a concentration of $3\times10^4$ cells/well and then cultured overnight (O/N) in a 37° C., $CO_2$ incubator. After the medium was removed from each well, LM1071 or LM1001 was diluted to each bacterial count in the medium and used for treatment for 2 hours. To induce inflammation of the RAW 264.7 cells, each well was treated with LPS and then further cultured for 24 hours in the 37° C., $CO_2$ incubator. The production amount of NO was measured with a Griess Reagent system from Promega, and 50 $\mu\ell$ of the cultured medium was transferred into a new 96-well plate. An NO standard solution was used after dilution to a concentration of 1.56 $\mu$M to 100 $\mu$M to generate an NO standard curve. Then, 50 $\mu\ell$ of a sulfanilamide solution was put into each well and allowed to react for 5 minutes at room temperature protected from light. Further, 50 $\mu\ell$ of an NED solution was added to each well and allowed to react for 5 minutes at room temperature protected from light. Then, the absorbance at 540 nm was measured with a microplate reader, and the production amount of NO was calculated based on the NO standard curve (see FIG. 2A, FIG. 2B).

According to the test result, it was confirmed that only LM1071 inhibits the excessive production of NO induced by LPS which is an inflammatory substance.

Example 2. Test for Immune-Boosting Ability and Anti-Inflammatory Ability when Treated with Mixed Strain of LM1071 and LM1001

(1) Test for Immune-Boosting Ability

Figure 3A:
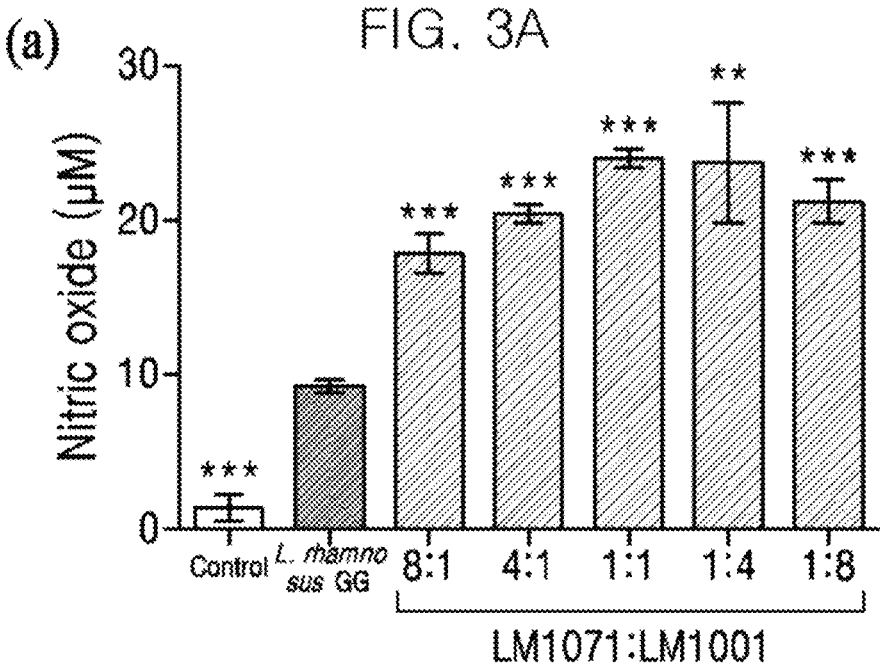
FIG. 3A shows the production amount of NO (immune-boosting ability) depending on a mixture ratio of the strain LM1071 and the strain LM1001 according to an embodiment of the present disclosure.

A DMEM medium (Welgene, Korea) made of 10% fetal bovine serum (FBS) (Welgene, Korea) and penicillin/streptomycin (Welgene, Korea) was used to culture RAW 264.7 cells, which are a murine macrophage cell line. The RAW 264.7 cells were seed in a 96-well plate at a concentration of $3\times10^4$ cells/well and then cultured overnight (O/N) in a 37° C., $CO_2$ incubator. After the medium was removed from each well, mixtures of LM1071 and LM1001 (LM1071: LM1001=8:1, 4:1, 1:1, 1:4 and 1:8) were diluted in the medium and used for treatment for 24 hours. Herein, *Lactobacillus rhamnosus* GG (hereinafter, referred to as "*L. rhamnosus* GG") was used for treatment of a positive control. The production amount of NO was measured with a Griess Reagent system from Promega, and 50 $\mu\ell$ of the cultured medium was transferred into a new 96-well plate. An NO standard solution was used after dilution to a concentration of 1.56 $\mu$M to 100 $\mu$M to generate an NO standard curve. Then, 50 $\mu\ell$ of a sulfanilamide solution was put into each well and allowed to react for 5 minutes at room temperature protected from light. Further, 50 $\mu\ell$ of an NED solution was added to each well and allowed to react for 5 minutes at room temperature protected from light. Then, the absorbance at 540 nm was measured with a microplate reader, and the production amount of NO was calculated based on the NO standard curve (see FIG. 3A).

According to the test result, it was confirmed that the mixtures of LM1071 and LM1001 in a ratio of 8:1 to 1:8 result in a greater production amount of NO than *L. rhamnosus* GG.

(2) Test for Anti-Inflammatory Ability

Figure 3B:
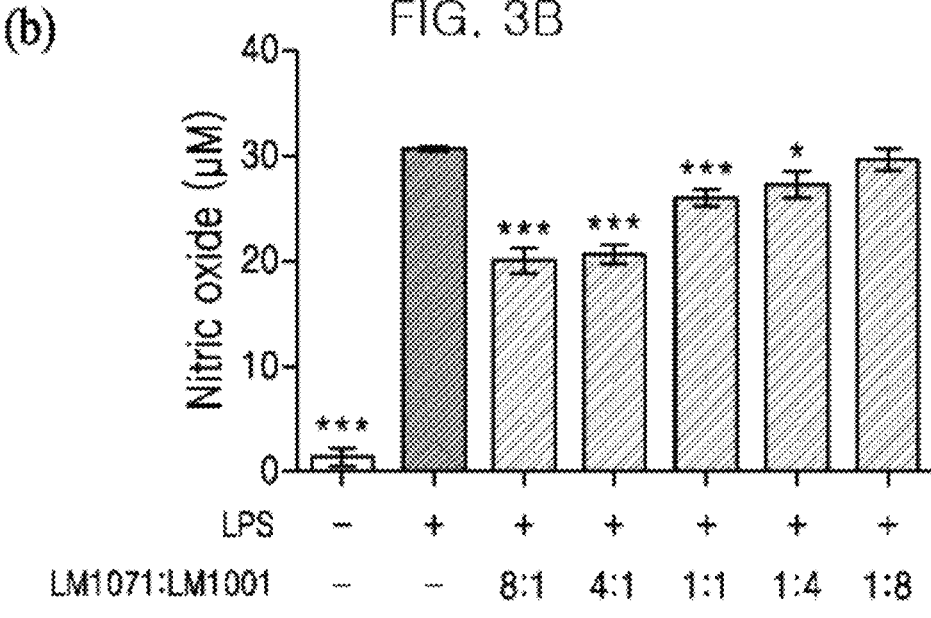
FIG. 3B shows the inhibition of production of NO induced by LPS (anti-inflammatory ability) depending on a mixture ratio of the strain LM1071 and the strain LM1001 according to an embodiment of the present disclosure.
Figure 4A:
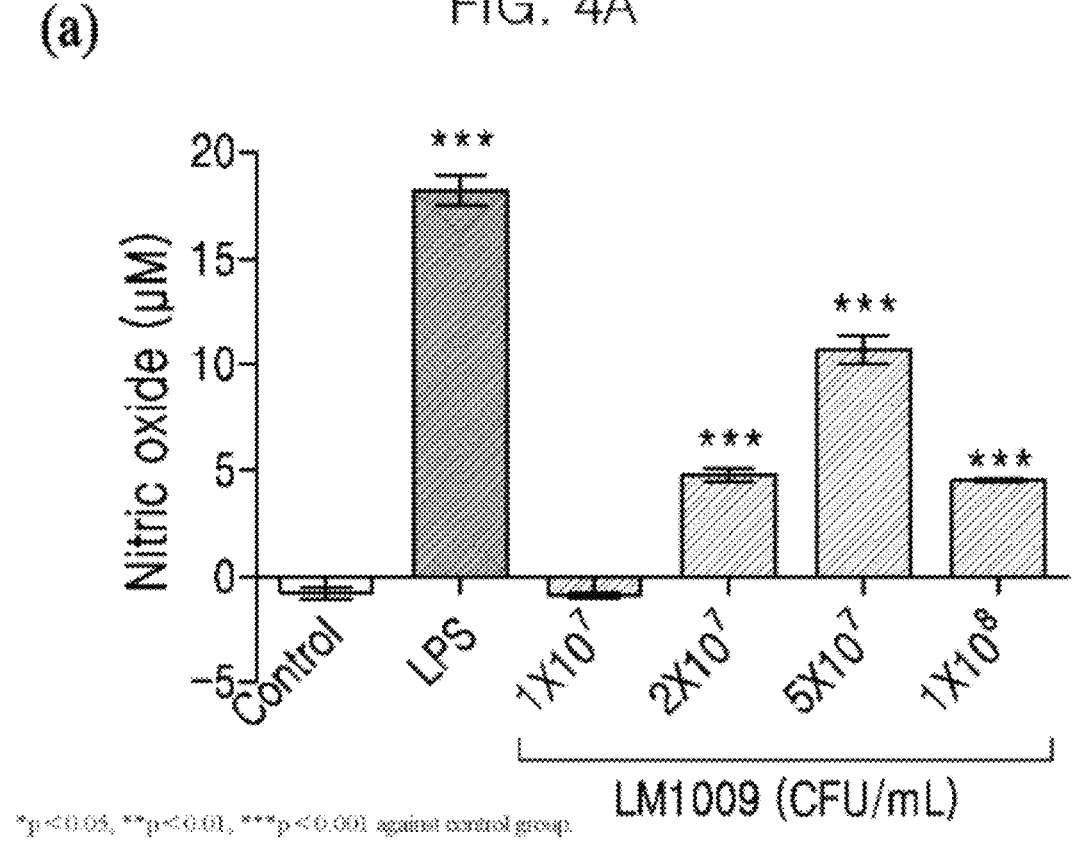
FIG. 4A shows the production amount of NO (immune-boosting ability) of LM1009 according to an embodiment of the present disclosure.
Figure 4B:
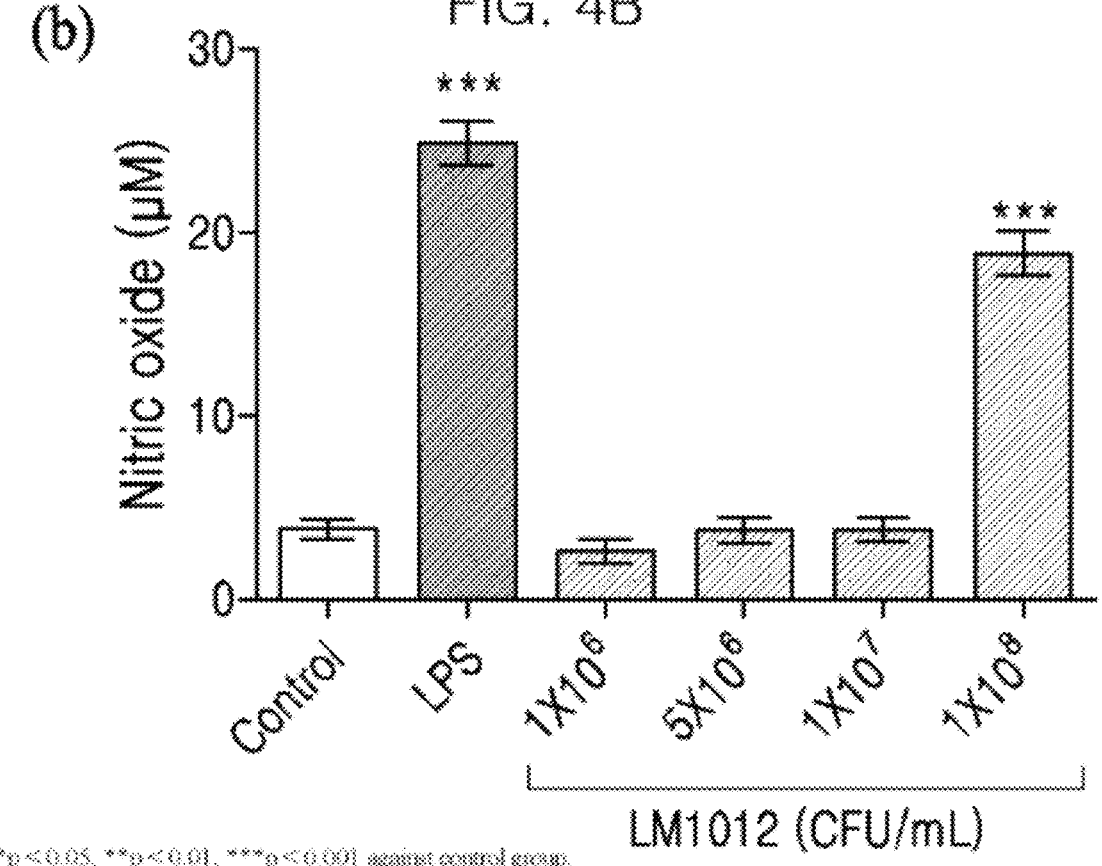
FIG. 4B shows the production amount of NO (immune-boosting ability) of LM1012 according to an embodiment of the present disclosure.
Figure 4C:
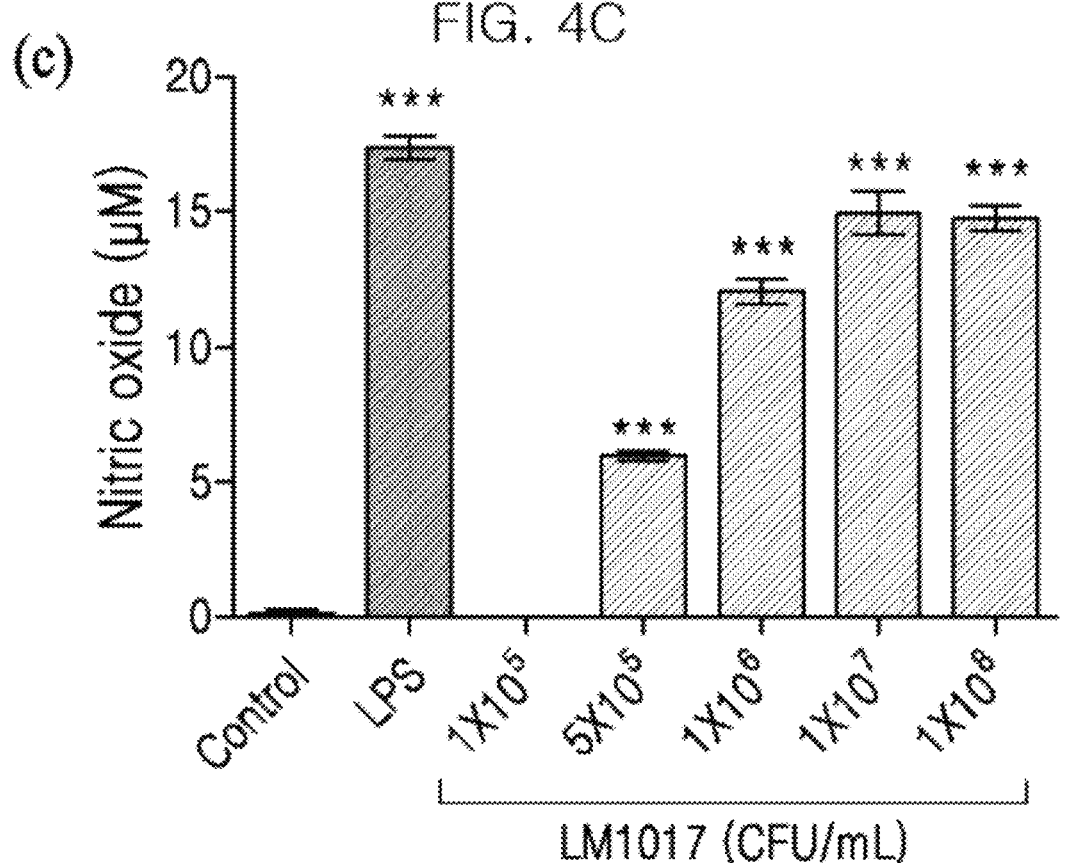
FIG. 4C shows the production amount of NO (immune-boosting ability) of LM1017 according to an embodiment of the present disclosure.
Figure 4D:
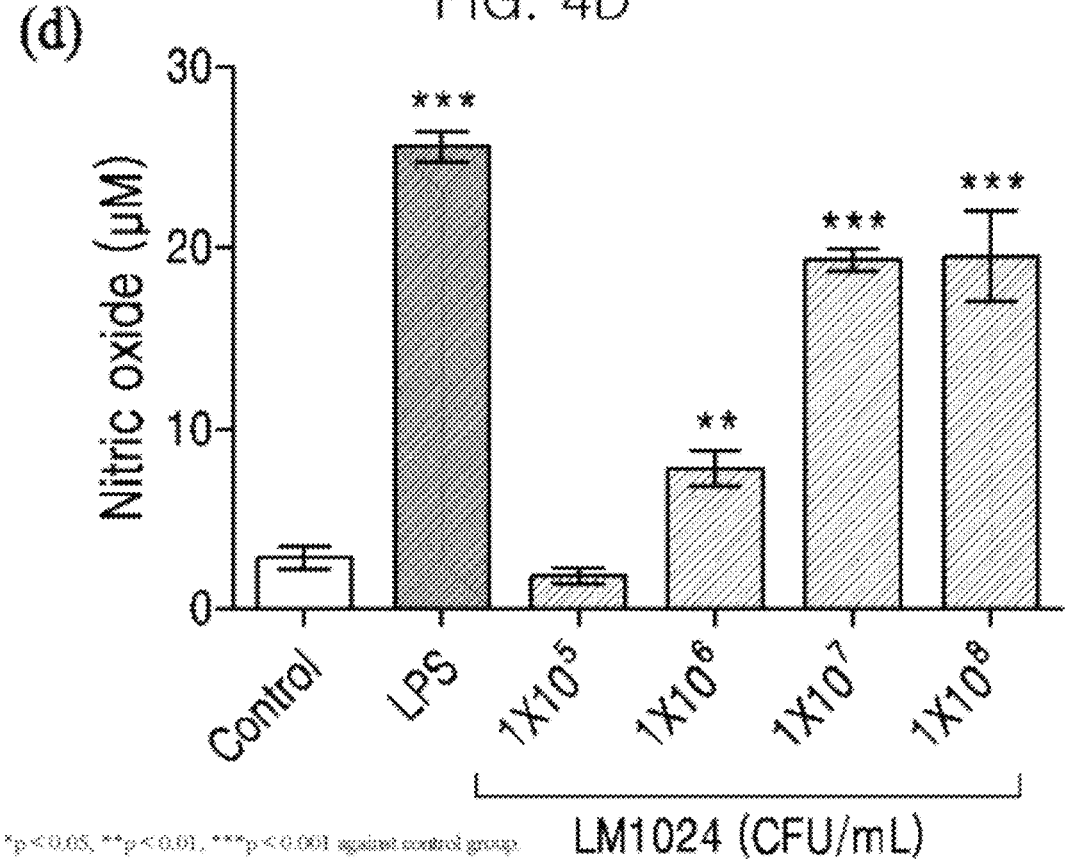
FIG. 4D shows the production amount of NO (immune-boosting ability) of LM1024 according to an embodiment of the present disclosure.
Figure 4E:
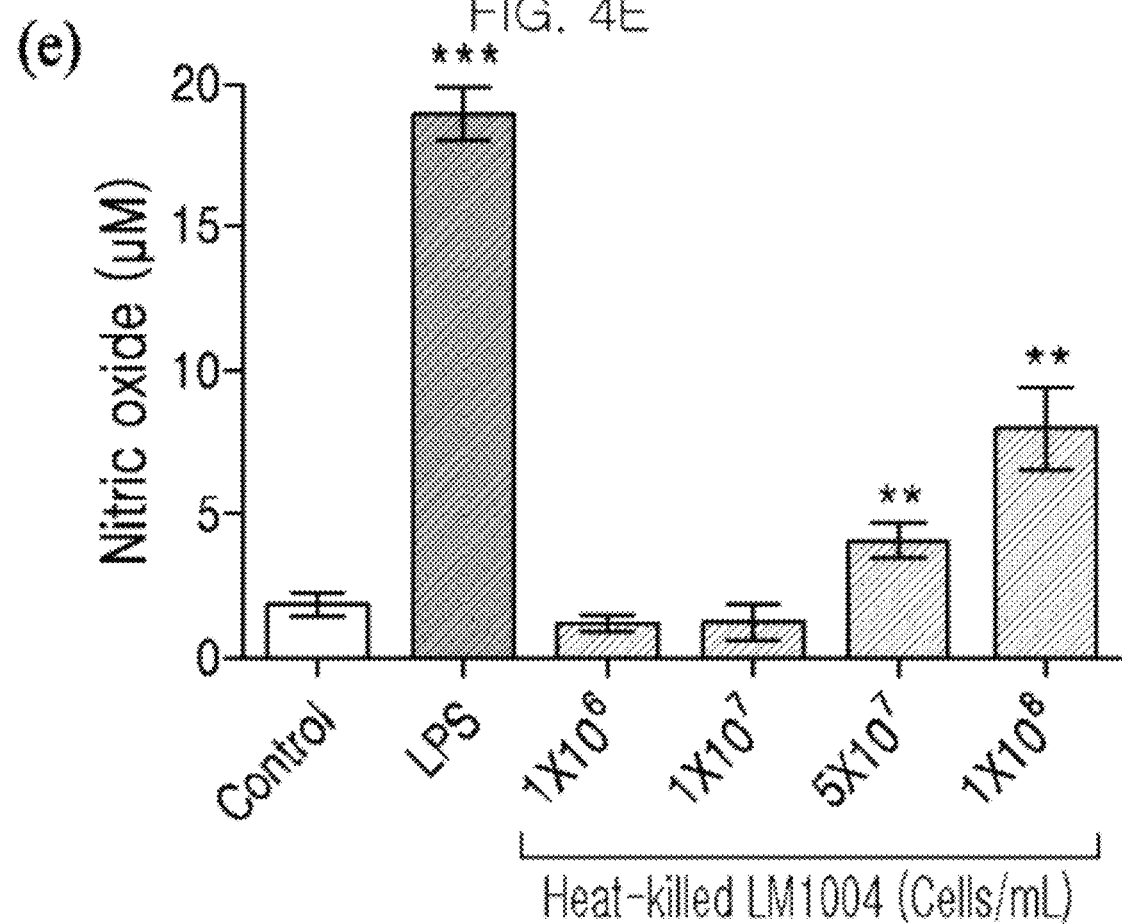
FIG. 4E shows the production amount of NO (immune-boosting ability) of heat-killed LM1004 according to an embodiment of the present disclosure.
Figure 5A:
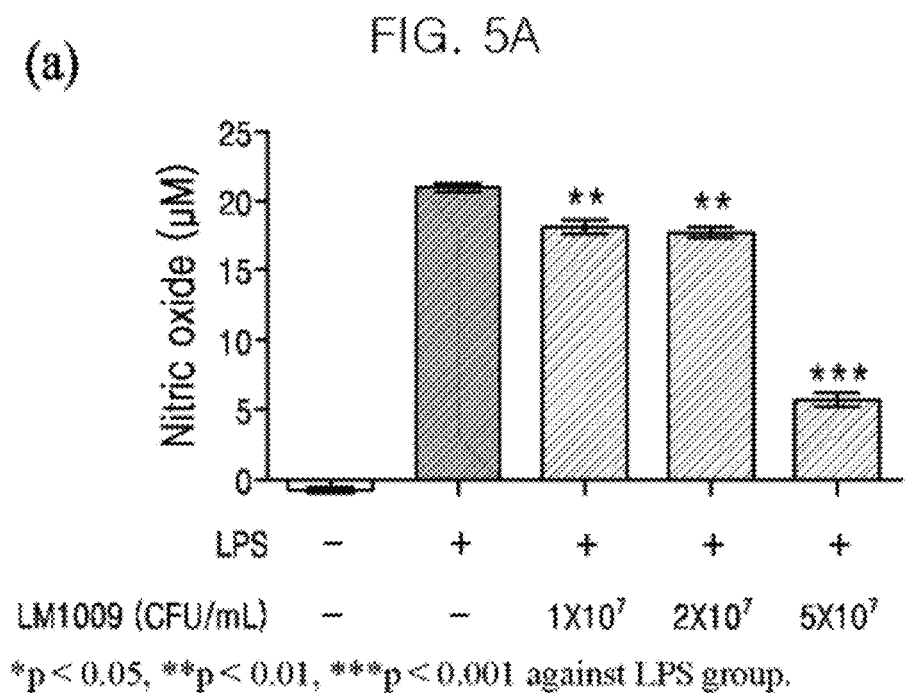
FIG. 5A shows the inhibition of production of NO induced by LPS (anti-inflammatory ability) when treated with LM1009 alone according to an embodiment of the present disclosure.
Figure 5B:
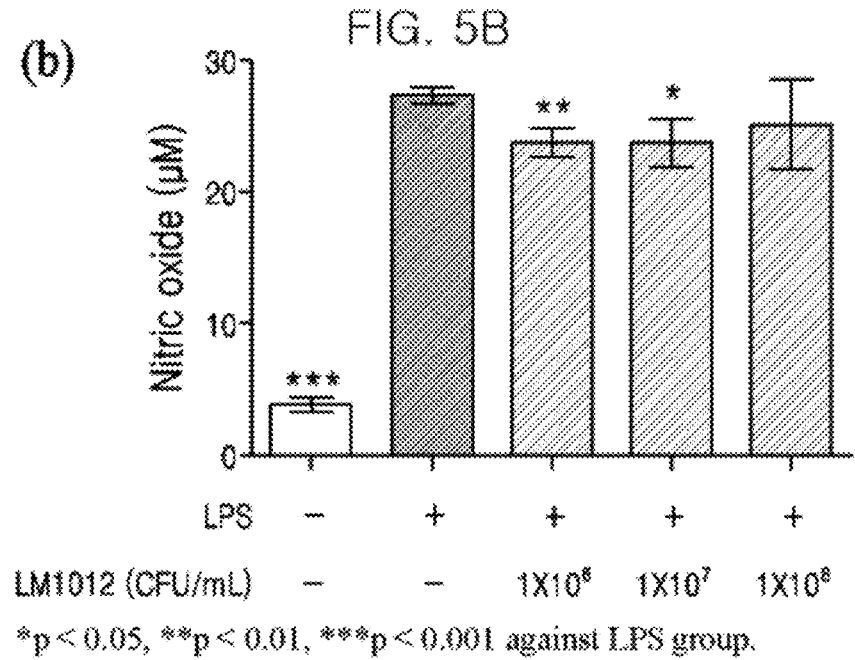
FIG. 5B shows the inhibition of production of NO induced by LPS (anti-inflammatory ability) when treated with LM1012 alone according to an embodiment of the present disclosure.
Figure 5C:
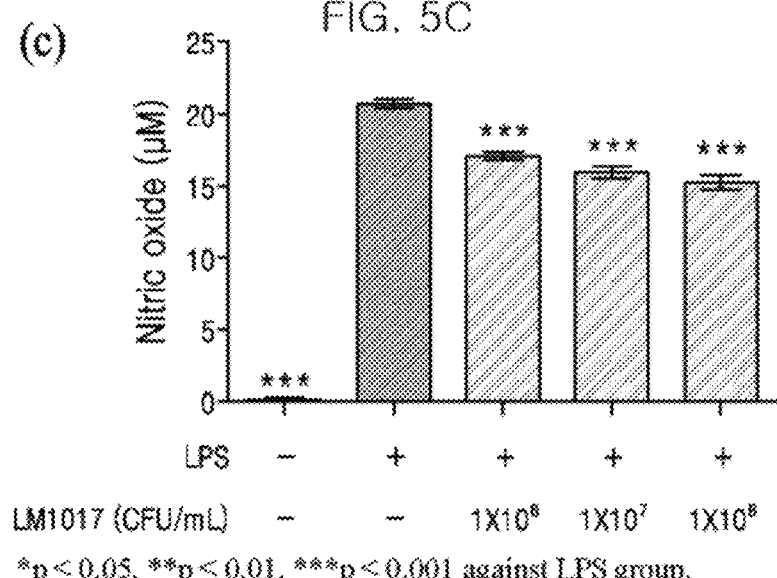
FIG. 5C shows the inhibition of production of NO induced by LPS (anti-inflammatory ability) when treated with LM1017 alone according to an embodiment of the present disclosure.
Figure 5D:
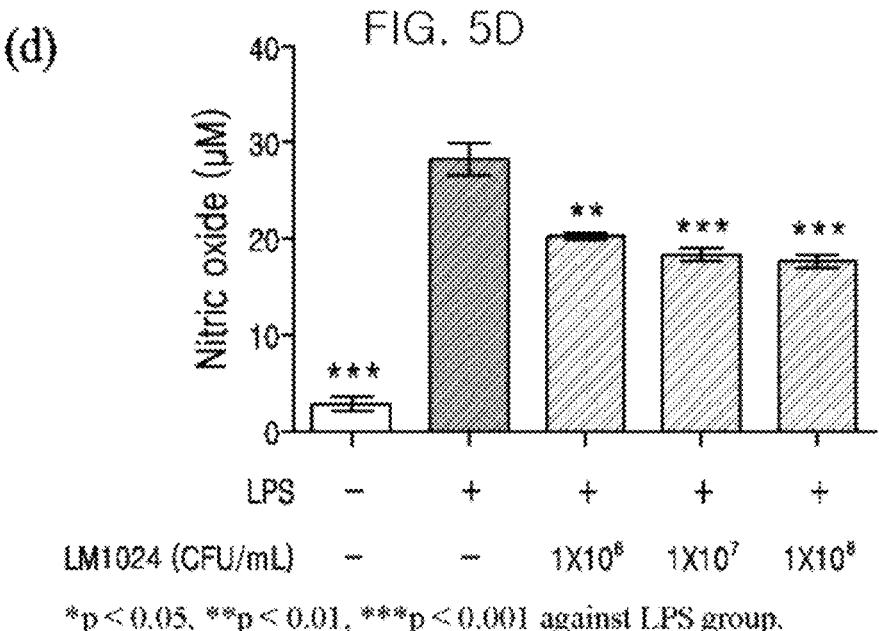
FIG. 5D shows the inhibition of production of NO induced by LPS (anti-inflammatory ability) when treated with LM1024 alone according to an embodiment of the present disclosure.
Figure 5E:
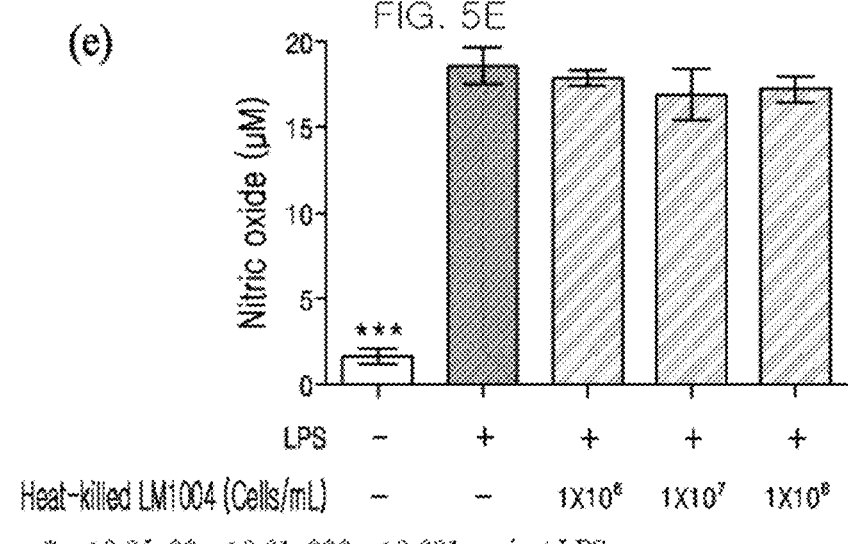
FIG. 5E shows the inhibition of production of NO induced by LPS (anti-inflammatory ability) when treated with heat-killed LM1004 alone according to an embodiment of the present disclosure.

A DMEM medium (Welgene, Korea) made of 10% fetal bovine serum (FBS) (Welgene, Korea) and penicillin/streptomycin (Welgene, Korea) was used to culture RAW 264.7 cells, which are a murine macrophage cell line. The RAW 264.7 cells were seed in a 96-well plate at a concentration of $3\times10^4$ cells/well and then cultured overnight (O/N) in a 37° C., $CO_2$ incubator. After the medium was removed from each well, mixtures of LM1071 and LM1001 (LM1071: LM1001=8:1, 4:1, 1:1, 1:4, and 1:8) were diluted in the medium and used for treatment for 2 hours. To induce inflammation of the RAW 264.7 cells, each well was treated with LPS and then further cultured for 24 hours in the 37° C., $CO_2$ incubator. The production amount of NO was measured with a Griess Reagent system from Promega, and 50 $\mu\ell$ of the cultured medium was transferred into a new 96-well plate. An NO standard solution was used after dilution to a concentration of 1.56 $\mu$M to 100 $\mu$M to generate an NO standard curve. Then, 50 $\mu\ell$ of a sulfanilamide solution was put into each well and allowed to react for 5 minutes at room temperature protected from light. Further, 50 $\mu\ell$ of an NED solution was added to each well and allowed to react for 5 minutes at room temperature protected from light. Then, the absorbance at 540 nm was measured with a microplate reader, and the production amount of NO was calculated based on the NO standard curve (see FIG. 3B).

According to the test result, it was confirmed that the mixtures of LM1071 and LM1001 in a ratio of 8:1 to 1:4 inhibit the production of NO induced by LPS when used for treatment in combination with LPS.

Overall, it can be seen that the mixtures of LM1071 and LM1001 have excellent immune-boosting ability in a mixture ratio of LM1071:LM1001 of 8:1 to 1:8 and excellent anti-inflammatory ability in a mixture ratio of LM1071: LM1001 of 8:1 to 1:4, and, thus, the mixtures of LM1071 and LM1001 have excellent immunoregulatory functions (immune-boosting ability and anti-inflammatory ability) in a mixture ratio of 8:1 to 1:4.

Example 3. Test of 5 Types of Strains for Immune-Boosting Ability and Anti-Inflammatory Ability (1) Test for Immune-Boosting Ability A DMEM medium (Welgene, Korea) made of 10% fetal bovine serum (FBS) (Welgene, Korea) and penicillin/streptomycin (Welgene, Korea) was used to culture RAW 264.7 cells, which are a murine macrophage cell line. The RAW 264.7 cells were seed in a 96-well plate at a concentration of $3\times10^4$ cells/well and then cultured overnight (O/N) in a 37° C., $CO_2$ incubator. After the medium was removed from each well, heat-killed bacteria of LM1009, LM1012, LM1071, LM1024, and LM1004 were diluted to each bacterial count in the medium and used for treatment for 24 hours. Herein, LPS was used for treatment of a positive control. The production amount of NO was measured with a Griess Reagent system from Promega, and 50 μℓ of the cultured medium was transferred into a new 96-well plate. An NO standard solution was used after dilution to a concentration of 1.56 μM to 100 μM to generate an NO standard curve. Then, 50 μℓ of a sulfanilamide solution was put into each well and allowed to react for 5 minutes at room temperature protected from light. Further, 50 μℓ of an NED solution was added to each well and allowed to react for 5 minutes at room temperature protected from light. Then, the absorbance at 540 nm was measured with a microplate reader, and the production amount of NO was calculated based on the NO standard curve (see FIG. 4A, FIG. 4B, FIG. 4C, FIG. 4D, FIG. 4E).

According to the test result, it was confirmed that all of the heat-killed bacteria of LM1009, LM1012, LM1017, LM1024, and LM1004 increase the production amount of NO.

(2) Test for Anti-Inflammatory Ability

A DMEM medium (Welgene, Korea) made of 10% fetal bovine serum (FBS) (Welgene, Korea) and penicillin/streptomycin (Welgene, Korea) was used to culture RAW 264.7 cells, which are a murine macrophage cell line. The RAW 264.7 cells were seed in a 96-well plate at a concentration of $3\times10^4$ cells/well and then cultured overnight (O/N) in a 37° C., $CO_2$ incubator. After the medium was removed from each well, heat-killed bacteria of LM1009, LM1012, LM1071, LM1024, and LM1004 were diluted to each bacterial count in the medium and used for treatment for 2 hours. To induce inflammation of the RAW 264.7 cells, each well was treated with LPS and then further cultured for 24 hours in the 37° C., $CO_2$ incubator. The production amount of NO was measured with a Griess Reagent system from Promega, and 50 μℓ of the cultured medium was transferred into a new 96-well plate. An NO standard solution was used after dilution to a concentration of 1.56 μM to 100 μM to generate an NO standard curve. Then, 50 μℓ of a sulfanilamide solution was put into each well and allowed to react for 5 minutes at room temperature protected from light. Further, 50 μℓ of an NED solution was added to each well and allowed to react for 5 minutes at room temperature protected from light. Then, the absorbance at 540 nm was measured with a microplate reader, and the production amount of NO was calculated based on the NO standard curve (see FIG. 5A, FIG. 5B, FIG. 5C, FIG. 5D, FIG. 5E).

According to the test result, it was confirmed that LM1009, LM1017, and LM1024 have anti-inflammatory ability by inhibiting the production of NO induced by LPS.

Based on the test results of Examples 1 to 3, three types of strains (LM1001, LM1012, and LM1004) having excellent immune-boosting ability and four types of strains (LM1071, LM1009, LM1017, and LM1024) having excellent anti-inflammatory ability were selected, and the selected strains were used for tests of Example 4.

Example 4. Test of 7 Types of Mixed Strains for Immune-Boosting Ability and Anti-Inflammatory Ability (1) Test for Immune-Boosting Ability A DMEM medium (Welgene, Korea) made of 10% fetal bovine serum (FBS) (Welgene, Korea) and penicillin/streptomycin (Welgene, Korea) was used to culture RAW 264.7 cells, which are a murine macrophage cell line. The RAW 264.7 cells were seed in a 96-well plate at a concentration of $3\times10^4$ cells/well and then cultured overnight (O/N) in a 37°

Figure 6A:
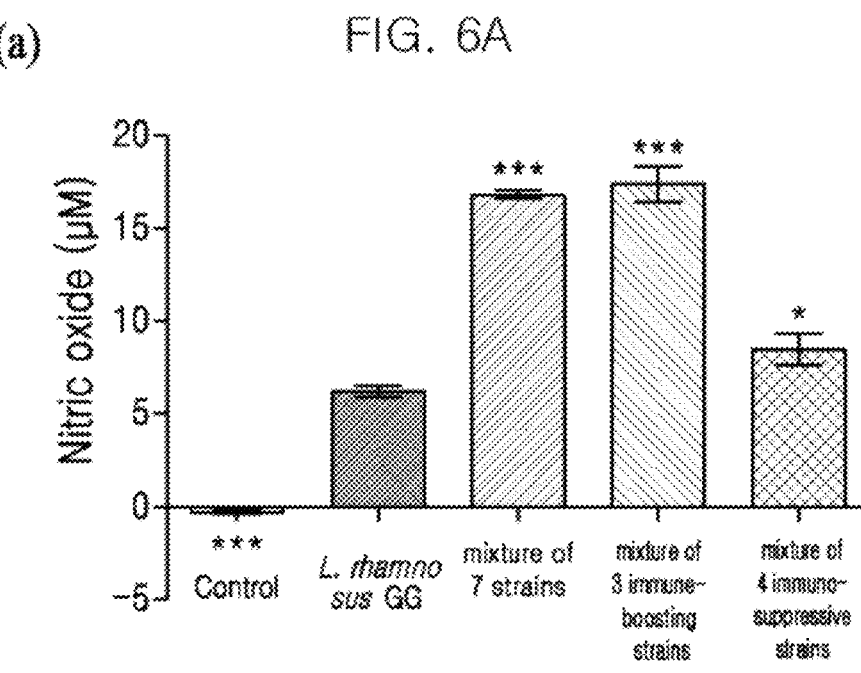
FIG. 6A shows the production amount of NO (immune-boosting ability) of a mixture of seven types of strains, a mixture of three types of immune-boosting strains (heat-killed bacteria of LM1001, LM1012, and LM1004), and a mixture of four types of immunosuppressive strains (heat-killed bacteria of LM1071, LM1009, LM1017, and LM1024) according to an embodiment of the present disclosure.

C., $CO_2$ incubator. After the medium was removed from each well, mixtures of strains (a mixture of seven types of strains, a mixture of three types of immune-boosting strains, and a mixture of four types of immunosuppressive strains) were diluted in the medium and used for treatment for 24 hours. Herein, *L. rhamnosus* GG was used for treatment of a positive control. The production amount of NO was measured with a Griess Reagent system from Promega, and 50 μℓ of the cultured medium was transferred into a new 96-well plate. An NO standard solution was used after dilution to a concentration of 1.56 μM to 100 μM to generate an NO standard curve. Then, 50 μℓ of a sulfanilamide solution was put into each well and allowed to react for 5 minutes at room temperature protected from light. Further, 50 μℓ of an NED solution was added to each well and allowed to react for 5 minutes at room temperature protected from light. Then, the absorbance at 540 nm was measured with a microplate reader, and the production amount of NO was calculated based on the NO standard curve (see FIG. 6A).

According to the test result, it was confirmed that the mixture of seven types of strains of the present disclosure results in a greater production amount of NO than the mixture of four types of immunosuppressive strains or *L. rhamnosus* GG.

(2) Test for Anti-Inflammatory Ability

Figure 6B:
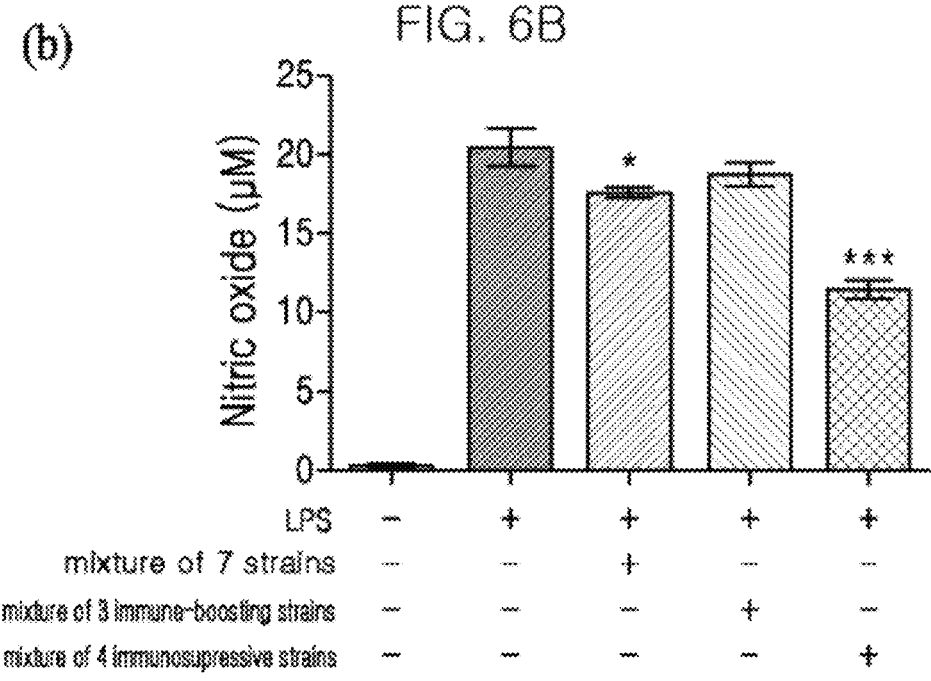
FIG. 6B shows the inhibition of production of NO induced by LPS (anti-inflammatory ability) of a mixture of seven types of strains, a mixture of three types of immune-boosting strains (heat-killed bacteria of LM1001, LM1012, and LM1004), and a mixture of four types of immunosuppressive strains (heat-killed bacteria of LM1071, LM1009, LM1017, and LM1024) according to an embodiment of the present disclosure.

A DMEM medium (Welgene, Korea) made of 10% fetal bovine serum (FBS) (Welgene, Korea) and penicillin/streptomycin (Welgene, Korea) was used to culture RAW 264.7 cells, which are a murine macrophage cell line. The RAW 264.7 cells were seed in a 96-well plate at a concentration of $3\times10^4$ cells/well and then cultured overnight (O/N) in a 37° C., $CO_2$ incubator. After the medium was removed from each well, mixtures of strains (a mixture of seven types of strains, a mixture of three types of immune-boosting strains, and a mixture of four types of immunosuppressive strains) were diluted in the medium and used for treatment for 2 hours. To induce inflammation of the RAW 264.7 cells, each well was treated with LPS and then further cultured for 24 hours in the 37° C., $CO_2$ incubator. The production amount of NO was measured with a Griess Reagent system from Promega, and 50 μℓ of the cultured medium was transferred into a new 96-well plate. An NO standard solution was used after dilution to a concentration of 1.56 μM to 100 μM to generate an NO standard curve. Then, 50 μℓ of a sulfanilamide solution was put into each well and allowed to react for 5 minutes at room temperature protected from light. Further, 50 μℓ of an NED solution was added to each well and allowed to react for 5 minutes at room temperature protected from light. Then, the absorbance at 540 nm was measured with a microplate reader, and the production amount of NO was calculated based on the NO standard curve (see FIG. 6B).

According to the test result, it was confirmed that the mixture of seven types of strains of the present disclosure further inhibits the excessive production of NO induced by an inflammatory substance compared to the mixture of three types of immune-boosting strains or the group treated with LPS alone.

Overall, it can be seen that the mixture of seven types of strains of the present disclosure can regulate immunity by increasing the production amount of NO (immune-boosting ability) or inhibiting the excessive production of NO induced by an inflammatory substance (anti-inflammatory ability).

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A composition, comprising:
*Lactobacillus reuteri* LM1071 deposited under accession number KCCM12650P;
*Lactobacillus plantarum* LM1001 deposited under accession number KCCM42959;
*Bifidobacterium animalis* subsp. *lactis* LM1017 deposited under accession number KCCM12629P;
*Bifidobacterium longum* LM1024 deposited under accession number KCCM12919P;
*Lactococcus lactis* LM1009 deposited under accession number KCCM80146;
*Streptococcus thermophilus* LM1012 deposited under accession number KFCC11771P; and
*Lactobacillus plantarum.*

2. The composition of claim 1,
wherein the *Lactobacillus reuteri* LM1071 and the *Lactobacillus plantarum* LM1001 contained in the composition have a mixture ratio of 8:1 to 1:4.

3. The composition of claim 1,
wherein the *Lactobacillus plantarum* is *Lactobacillus plantarum* LM1004 deposited under accession number KCCM43246.

4. A food composition for regulating immunity, comprising:
*Lactobacillus reuteri* LM1071 deposited under accession number KCCM12650P;

*Lactobacillus plantarum* LM1001 deposited under accession number KCCM42959;
*Bifidobacterium animalis* subsp. *lactis* LM1017 deposited under accession number KCCM12629P;
*Bifidobacterium longum* LM1024 deposited under accession number KCCM12919P;
*Lactococcus lactis* LM1009 deposited under accession number KCCM80146;
*Streptococcus thermophilus* LM1012 deposited under accession number KFCC11771P; and
*Lactobacillus plantarum.*

5. The food composition of claim 4,
wherein the *Lactobacillus reuteri* LM1071 and the *Lactobacillus plantarum* LM1001 contained in the food composition have a mixture ratio of 8:1 to 1:4.

6. The food composition of claim 4,
wherein the *Lactobacillus plantarum* is *Lactobacillus plantarum* LM1004 deposited under accession number KCCM43246.

7. A pharmaceutical composition for preventing or treating immune-related diseases, comprising:
*Lactobacillus reuteri* LM1071 deposited under accession number KCCM12650P;
*Lactobacillus plantarum* LM1001 deposited under accession number KCCM42959;
*Bifidobacterium animalis* subsp. *lactis* LM1017 deposited under accession number KCCM12629P;
*Bifidobacterium longum* LM1024 deposited under accession number KCCM12919P;
*Lactococcus lactis* LM1009 deposited under accession number KCCM80146;
*Streptococcus thermophilus* LM1012 deposited under accession number KFCC11771P; and
*Lactobacillus plantarum.*

8. The pharmaceutical composition of claim 7,
wherein the *Lactobacillus reuteri* LM1071 and the *Lactobacillus plantarum* LM1001 contained in the pharmaceutical composition have a mixture ratio of 8:1 to 1:4.

9. The pharmaceutical composition of claim 7,
wherein the *Lactobacillus plantarum* is *Lactobacillus plantarum* LM1004 deposited under accession number KCCM43246.

* * * * *